United States Patent [19]
Vock et al.

[11] Patent Number: 5,016,634
[45] Date of Patent: May 21, 1991

[54] IMPLANTABLE MEDICAL DEVICE WITH MEANS FOR TELEMETRIC TRANSMISSION OF DATA

[75] Inventors: Josef Vock, Spanga; Jan Ljungstroem, Solna; Christer Ekwall, Spanga, all of Sweden

[73] Assignee: Siemens Aktiengesellschaft, Berlin and Munich, Fed. Rep. of Germany

[21] Appl. No.: 505,509

[22] Filed: Apr. 6, 1990

[30] Foreign Application Priority Data

Apr. 18, 1989 [EP] European Pat. Off. ......... 89106275.4

[51] Int. Cl.⁵ ............................................. A61N 1/37
[52] U.S. Cl. ............................................. 128/419 PT
[58] Field of Search ................................ 128/419 PG

[56] References Cited
U.S. PATENT DOCUMENTS

| 4,374,382 | 2/1983 | Markowitz | 128/419 PT |
| 4,556,063 | 12/1985 | Thompson et al. | 128/419 PT |
| 4,571,589 | 2/1986 | Slocum et al. | 128/419 PT |
| 4,681,111 | 7/1987 | Silvian | 128/419 PT |
| 4,705,043 | 11/1987 | Imran | 128/419 P |
| 4,867,163 | 9/1989 | Schaldach | 128/419 PG |

FOREIGN PATENT DOCUMENTS 0120250 4/1987 European Pat. Off. .

Primary Examiner—William E. Kamm
Attorney, Agent, or Firm—Hill, Van Santen, Steadman & Simpson

[57] ABSTRACT

A medical device adapted to be implanted in a patient includes components for detecting physiological events and/or for stimulating physiological events, and includes control logic connected to the detecting and or stimulating components, and further components for the telemetric transmission of data relating to the logical status of the control logic to and from an external receiver. The components for telemetrically transmitting data are connected to the control logic, and continuously transmit data identifying the current logical status of the control logic to the external receiver.

9 Claims, 3 Drawing Sheets

IMPLANTABLE MEDICAL DEVICE WITH MEANS FOR TELEMETRIC TRANSMISSION OF DATA

BACKGROUND OF THE INVENTION

1. Field of the Invention

The present invention is directed to medical devices of the type implantable in the body of a patient, and in particular to such devices having means for detecting physiological events and/or means for stimulating physiological events, and control logic to which the means for detecting and/or the means for stimulating are connected, and means for the telemetric transmission of data relating to the logic status of the control logic to an external receiver, the means for transmission of data being connected to the control logic.

2. Description of Prior Art

Devices of the type described above are known, for example, heart pacemaker or defibrillators, wherein the logic status of the control logic is dependent, among other things, on whether a physiological event was detected, or whether a physiological event was stimulated. When the physiological functions of the patient in which the events are detected and/or stimulated are represented as a function of time, i.e., as an electrocardiogram, and when the data relating to the logic status of the control logic are generated with those events in the correct chronological correspondence, it is possible to evaluate the interaction of the implanted device with the body of the patient. It is known to accomplish a readout of the logic status data non-evasively by the telemetric transmission of this data to an external receiver.

A device of this type is described in European published Application 0 120 250. This device is a heart pacemaker which stores data regarding a preceding heart or pacemaker cycle, and transmits the data to the receiver with a delay, namely when an event which terminates the cycle occurs. The data transmission thus ensues with a delay corresponding to the duration of a cycle. To represent the transmitted data in correct chronological allocation to an electrocardiogram of the patient, it is thus necessary to delay the representation of the electrocardiogram, which requires considerable outlay. Moreover, transmission of the data with respect to each cycle occurs only once. The risk of data loss is thus high. An effective correction of data transmission errors in the receiver is possible only to the extent that data which is obviously senseless can be suppressed.

Another device of this type is described in U.S. Pat. No. 4,374,382. In this known device, the detection of a physiological event or the stimulation of a physiological event causes the formation and transmission of a code corresponding to the event. The data transmission ensues quasi-simultaneously with the appearance of the event. Again, however, data transmission ensues only a single time per event. The risk of data loss is again high, and an effective error correction with respect to the transmitted data is not possible.

SUMMARY OF THE INVENTION

It is an object of the present invention to provide an implantable device which detects and/or stimulates physiological events under the control of control logic, and which telemetrically transmits data relating to the logic status of the control logic to an external receiver, wherein the data transmission takes place with high reliability, the risk of data losses is reduced, and the possibility of effective correction of data transmission errors is provided.

The above object is achieved in accordance with the principles of the present invention wherein the means for transmitting data continuously transmit the data corresponding to the logical status of the control logic. As a consequence of the continuous data transmission, there is no direct linkage of the data transmission event with the detection or stimulation of the physiological events. The data regarding a defined logic status of the control logic can thus be transmitted multiply, which considerably increases the reliability of the data transmission and simultaneously makes possible the correction of data transmission errors. The transmission of current data also avoids the delay of the data transmission relative to the status of the control logic. The data transmission can ensue in both analog and digital form. In the case of analog data transmission, for example, frequency modulation can be used. A defined frequency, with which the means for transmitting data modulate a carrier signal upon occurrence of the corresponding logic status, is then allocated to every possible logic status of the control logic. A complete continuous data transmission occurs in this case, whereas in the case of digital transmission of data only a quasi-continuous data transmission occurs. Such quasi-continuous data transmission, however, offers the same advantages as a continuous data transmission given a sufficiently rapid succession of the individual dat transmissions. An advantage of the quasi-continuous data transmission over the continuous data transmission is that the former is less technically complex.

In a preferred embodiment of the invention, a clock generator is provided which activates the means for transmitting data so that data is transmitted at continuously successive points in time. The means for transmitting data transmit data which are current at the point in time of the data transmission. The data transmission again occurs independently of detected physiological events and independently of stimulated physiological events, because the clock generator for the activation of the data transmission means transmits data at periodically successive points in time. The means for transmission of data can be activated (enabled) as often as is desired with the clock generator, within the limits placed thereon by the maximum data transmission rate of the data transmission means and the data set which is to be transmitted for each data transmission. A quasi-continuous data transmission thus results, wherein the means for the transmission of data are multiply activated during the duration of a logical state, given a suitable selection of the duration of the time intervals between successive points in time of data transmission. The data corresponding to a defined logical state are thus multiply transmitted, so that data losses are virtually impossible. The multiple transmission of data, moreover, also provides the precondition for an effective correction of data transmission errors because, for example, there is the possibility of constructing the receiver so that it accepts only data which are transmitted unmodified over multiple successive transmissions. The device herein may be of the type which is cyclicly operated through successive device cycles, in which case a further embodiment of the invention can be undertaken wherein the clock generator multiply activates the means for the transmission of data during a device cycle. Even if the logic status of the control logic changes rapidly during a device cycle, it is thus insured that the transmission of the corresponding data occurs with high reliability. Although it is theoretically possible within the scope of the present invention to have the clock generator activate the data transmission means only once during a device cycle, such operation is only useful if the data to be transmitted correspond to a logic status of the control logic which usually remains unchanged over a plurality of device cycles.

Although it is possible to undertake parallel transmission in accordance with the principles of the present invention, a further embodiment is disclosed herein in which the transmission of data occurs serially. Since the data transmission does not occur through a hard-wired connection, but instead occurs telemetrically, the technological and cost outlay for the device can be considerably reduced using serial data transmission.

In a further embodiment of the invention, the device may be a heart pacemaker, and the means for detecting physiological events may be means for monitoring the electrical activity of the heart, and the means for stimulating physiological events may be means for electrically stimulating the heart. The means for detecting physiological events may form an electrical signal corresponding to the associate physiological event, i.e. an electrical signal corresponding to the electrical activity of the heart in the case of a heart pacemaker, which is supplied to an analog-to-digital converter whose digital output signal is then supplied to the data transmission means, which in turn transmit the digital output signal to the external receiver. Because the means for transmitting data, the means for detecting physiological events, and thus the means for forming the electrical signal corresponding the physiological function, are already present, data corresponding to the physiological function in the form an intracardial electrogram (IEKG) in the case of a heart pacemaker can be acquired in a simple manner and transmitted to the receiver. The means for transmitting data may also be supplied with further data relating to the operating condition of the implanted device, in addition to being supplied with the data relating to the logic status of the control logic. Both data sets can then be transmitted to the receiver via the telemetric transmission means. This permits the proper technological functioning of the implanted device to be checked in a simple manner. For this purpose, in a further embodiment of the invention the means for the transmission of data transmits data corresponding to the logic status of the control logic as well as the digital output signals of the analog-to-digital converter, or the data relating to the operating condition of the device, in the form of a single data word. In this embodiment, an interconnected bit sequence of the data word contains the data corresponding to the logic state of the control logic and the digital output signals of the analog-to-digital converter. This insures that the correct chronological allocation of the signals corresponding to the logic status of the control logic to the signal corresponding to the electrical activity of the heart, i.e. the IEKG, is insured without special measures.

DESCRIPTION OF THE PREFERRED EMBODIMENTS

Figure 1:
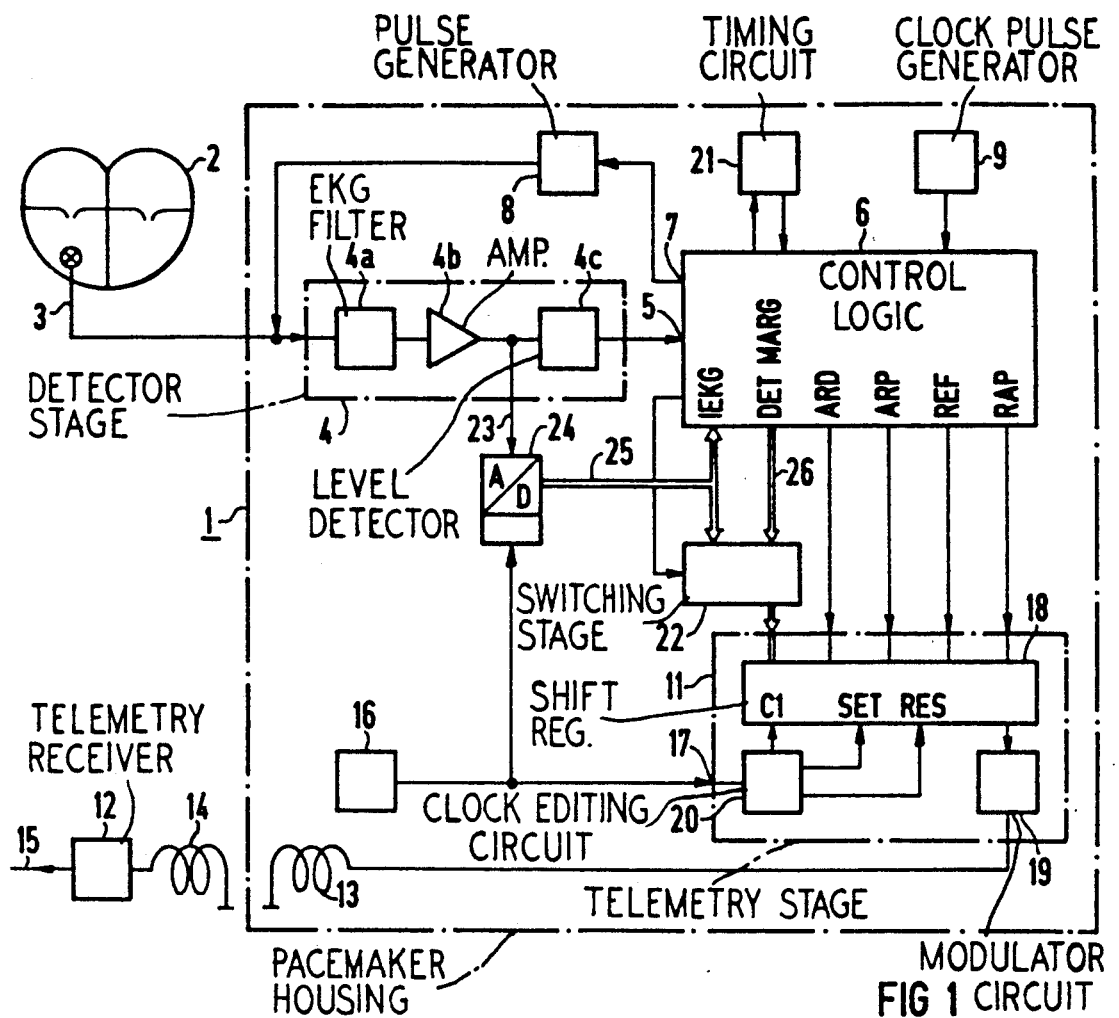
FIG. 1 is a schematic block diagram of a heart pacemaker constructed in accordance with the principles of the present invention.

An implantable medical device constructed in accordance with the principles of the present invention is shown in FIG. 1, this device being shown for exemplary purposes as a heart pacemaker. The pacemaker includes a pacemaker housing 1, and may operate in the VVI mode. The components contained within the pacemaker housing 1 are in communication with the heart 2 of a patient via an electrode 3 inserted, for example, into the ventricle of the heart 2.

The electrode 3 serves the purpose of acquiring a signal corresponding to the electrical activity of the heart 2 and supplying that signal to the components contained within the pacemaker housing 1. Within the pacemaker housing 1, the signal proceeds to a detector stage 4, which includes an EKG filter 4a, an amplifier 4b, and a level detector circuit 4c. If the output signal from the amplifier 4b has a minimum amplitude corresponding to that of a natural heartbeat and/or a defined steepness typical of a natural heartbeat, the level detector 4c generates a digital signal indicating the detection of a natural heartbeat. The output of the detector stage 4 is supplied to an input 5 of control logic 6. The control logic 6 makes a determination on the basis of the incoming digital signals, and based on stored data, as to whether, and when, an artificial stimulation of the heart 2 should occur. If artificial stimulation of the heart 2 is necessary, the control logic 6 generates a signal at an output 7 at an appropriate time to a stimulation pulse generator 8. The stimulation pulse generator 8 then generates a stimulation pulse having a defined amplitude and duration.

The electrode 3 also serves the purpose of supplying these stimulation pulses to the heart 2, and accordingly the output of the stimulation pulse generator 8 is connected to the electrode 3.

All timing signals required for the functioning of the control logic 6 are acquired from the signal of a clock generator 9. The clock generator 9 may be, for example, a crystal oscillator and is connected to a clock input of the control logic 6. A timing circuit 21 is also connected to the control logic 6. The timing circuit 21 begins the measurement of a defined chronological duration simultaneously with the enabling of the stimulation pulse generator 8. The defined chronological duration corresponds to a maximally allowable repetition rate of the stimulation pulses. As long as the defined chronological duration has not expired, the control logic 6 suppresses the generation of a further stimulation pulse. In the event of a malfunction of the clock generator 9, it is thus avoided that the repetition of the stimulation pulses could occur at a rate which is physiologically dangerous to the patient.

The control logic 6 has a series of outputs respectively referenced REF ARD ARP RAP. Each of these outputs can respectively assume either the status of a logic "1" or a logic "0". The output REF has the status of a logic "1" as long as the technical refractory time is running. The output ARD has the status of a logic "1" as soon as a natural heartbeat is detected, and remains in this state as long as the absolute technical refractory time is running. The output ARP assumes the state of a logic "1" as soon as a stimulation pulse is generated, and remains in this state for the duration of the absolute refractory time. When the timing circuit 21 is started, the output ARP assumes the status of a logic "1" and remains in this state for the duration of the defined chronological duration so that a check can be undertaken to determine whether the timing circuit 21 is functioning correctly.

The terms "technical refractory time" and "absolute refractory time," which are standard terminology in the heart pacemaker technology, can be derived from the applicable literature such as, for example, the instruction manual (October, 1986) for the DIALOG Pacemaker 728, manufactured by Siemens-Elema AB, Solna, Sweden.

Data corresponding to a momentary logic state of the control logic are thus available at the aforementioned outputs of the control logic 6. If the data are represented, for example, in suitable form and in correct chronological allocation to an electrocardiogram, the data can provide important information about the interaction of the pacemaker with the heart 2.

For this purpose, a telemetry circuit 11 is provided in the pacemaker housing 1, and is connected to the aforementioned outputs of the control logic 6. The telemetry circuit 11 permits the data corresponding to the logic status of the control logic 6 to be transmitted from the pacemaker housing 1, implanted in a patient to an external receiver 12. The transmission of data occurs non-invasively by inductive data transmission. For this purpose, the output of the telemetry circuit 11 is connected to a transmission coil 13. When data transmission is desired, a reception coil 14, connected to the telemetry receiver 12, connected to the telemetry receiver 12, is brought into proximity with the transmission coil 13, so that the coils 13 and 14 are inductively coupled.

The data which are received by the telemetry receiver 12 can be supplied via an output 15 to an EKG recorder, or to any other device suitable for the evaluation or portrayal of the data.

As can be seen in FIG. 1, a clock generator 16 is provided which generates a clock signal that is supplied to a clock input 17 of the telemetry circuit 11. The clock generator 16 is an oscillator which generates a signal having a constant period. Such circuits are well known to those skilled in the electronics art. The signal supplied to the clock input 17 of the telemetry circuit 11 continuously activates (enables) the telemetry circuit 11 for the transmission of data corresponding to the logic status of the control logic 6, i.e. at periodically successive points in time.

The telemetry circuit 11 contains a shift register 18 having parallel inputs, the inputs of the shift register 18 being respectively connected to the outputs of the control logic 6. The shift register 18 has a serially output which is connected to the transmission coil 13 via a modulator circuit 19. The modulator circuit 19 may be, for example, an FSK modulator. The signal supplied to the telemetry circuit 11 at the clock input 17 is edited by a clock editing circuit 20 so that it controls the shift register 18 so that the shift register 18 stores the data corresponding to the logic states at its parallel inputs immediately before the beginning of a data transmission. The data corresponding to the logic states is then serially supplied to the modulator circuit 19. The clock editing circuit 20 thus generates the necessary parallel input clock pulses, reset clock pulses and shift clock pulses which are normally required for the operation of a shift register, such as the shift register 18. These signals are supplied to respective inputs of the shift register 18 references SET RES and Cl. The output signal from the modulator circuit 19 proceeds via the transmission coil 13 and the reception coil 14 to the receiver 12, and is demodulated in the receiver in a suitable manner so as to be available at the output 15 of the receiver 12 a serial data stream.

The transmission of data corresponding to the logic state of the control logic 6 in the pacemaker housing 1 thus ensues independently of the appearance of any physiological events. The data transmission is thus independent of, for example, the detection of a natural heartbeat or the generation of a stimulation pulse, and ensues quasi-continuously at periodically successive points in time. Data which are current at the beginning of a data transmission are thus transmitted.

As is known, a heart pacemaker has a cyclical functioning which is undertaken in successive device cycles. The shortest possible cycle duration is the duration of the technical refractory time. The longest possible cycle duration is defined by the period of the frequency at which the heart pacemaker stimulates the heart as needed. The total duration of the technical refractory time is usually in the range of 200–500 ms. The clock frequency of the clock generator 16 is selected such that a plurality of data transmissions occur during a device cycle, i.e. during the running of the technical refractory time. If it is assumed that at least 30 data transmission should occur during a device cycle, in order to have sufficient reliable data transmission, data transmission must therefore ensue at intervals of at most 8 ms, based on a technical refractory time of 240 ms.

As can be seen in FIG. 1, the filtered and amplified signal of the electrode 3 is supplied to an analog-to-digital converter 24. The analog to digital converter 24 has a resolution of, for example, six bits, and receives its clock signals from the clock generator 16. The amplified and filtered signal corresponds to an intracardial electrogram (IEKG). This signal, in digital form, is conducted from the analog-to-digital converter 24 via a six bit-wide data bus 25 to an electronic switching stage 22 and to an IEKG input of the control logic 6. When the switching stage 22 is actuated by the control logic 6 via a control line 23, the output data of the analog-to-digital converter 24 proceed to the telemetry stage 11. For this purpose, the switching stage 22 is connected to an input of the shift register 18 in the telemetry stage 11 by a ten bit-wide bus. The shift register 18 transmits the data corresponding to the IEKG in common with the data corresponding to the logic status of the control logic 6.

Figure 2:
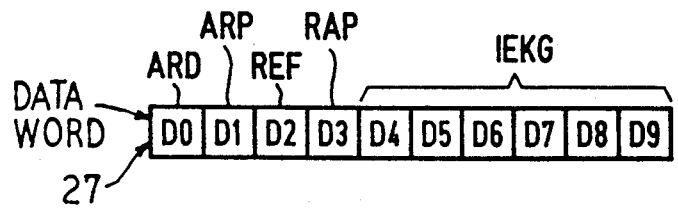
FIGS. 2 and 3 show respective data word formats for data which are transmitted by the heart pacemaker shown in FIG. 1.

As shown in FIG. 2, the aforementioned data transmission occurs in a single data word 27 having ten bits D0 through D9, with an interrelated sequence of six bits of the data word 27 containing the digital output signals of the analog to digital converter 24 corresponding to the IEKG, and an interrelated sequence of four bits of the data word 27 contains the data corresponding to the logic status of the control logic 6.

Figure 3:
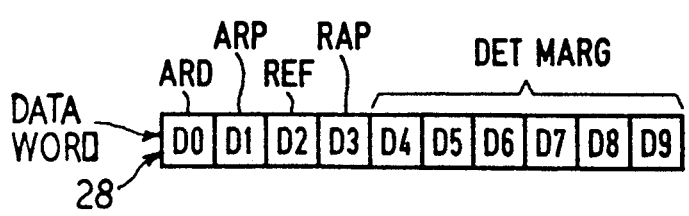

For every detected, natural heartbeat, the control logic 6 uses the digital output signals of the analog-to-digital converter 24, and the minimum amplitude that the signal corresponding to the electrical activity of the heart 2 should have in order to result in the detection of a natural heartbeat by the level detector 4c, to calculate was is referred to as the detection margin. The detection margin is an indication of the extent to which the amplitude of the signal corresponding to the electrical activity of the heart 2 exceeds the minimum amplitude in the detection of a natural heartbeat. The detection margin is an important value for evaluating the operating condition of the heart pacemaker to determine whether the established value of the minimum amplitude has been selected s that all naturally occurring heartbeats can be detected with high probability. If the detection margin is too low, a correction of the value of the minimum amplitude must ensue. Data corresponding to the detection margin are available at the output of the control logic 6 referenced DET MARG, and are supplied to the switching stage 22 via a six bit-wide data bus 26. When the control logic 6 activates the switching stage 22 via the control line 23 in suitable fashion, the digital data corresponding to the detection margin proceed the shift register 18 in the telemetry stage 11, instead of the data from the analog to digital converter 24. The telemetry stage 11 then transmits the data corresponding to the detection margin in common with the data corresponding to the logic state of the control logic 6. As shown in FIG. 3, this occurs in a single data word 28, having ten bits D0 through D9, with an interrelated sequence of six bits of the data word 28 containing the data corresponding to the detection margin, and an interrelated sequence of four bits of the data word containing the data corresponding to the logic state of the control logic 6.

It is also possible for the control logic 6 to activate the switching stage 22 so that the switching stage 22 functions as a multiplexer, with the telemetry stage 11 transmitting a data word 27 in alternation with a data word 28.

In addition to the aforementioned data, synchronization pulses and stop bits may be transmitted to the receiver 12 under certain circumstances in a known manner which is not shown in detail.

Figure 4:
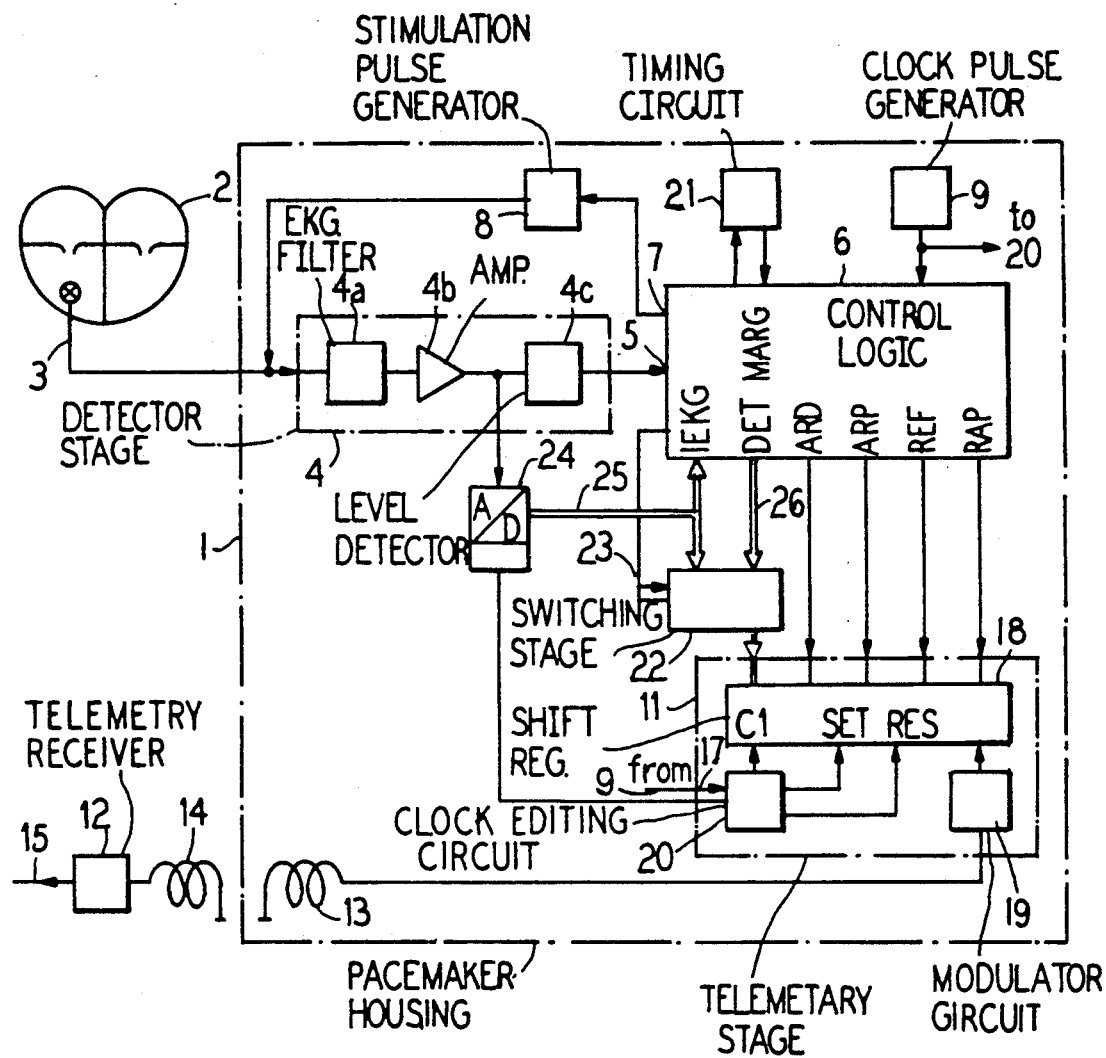
FIGS. 4 and 5 are schematic block diagrams of respective embodiments of a heart pacemaker constructed in accordance with the principles of the present invention.
Figure 5:
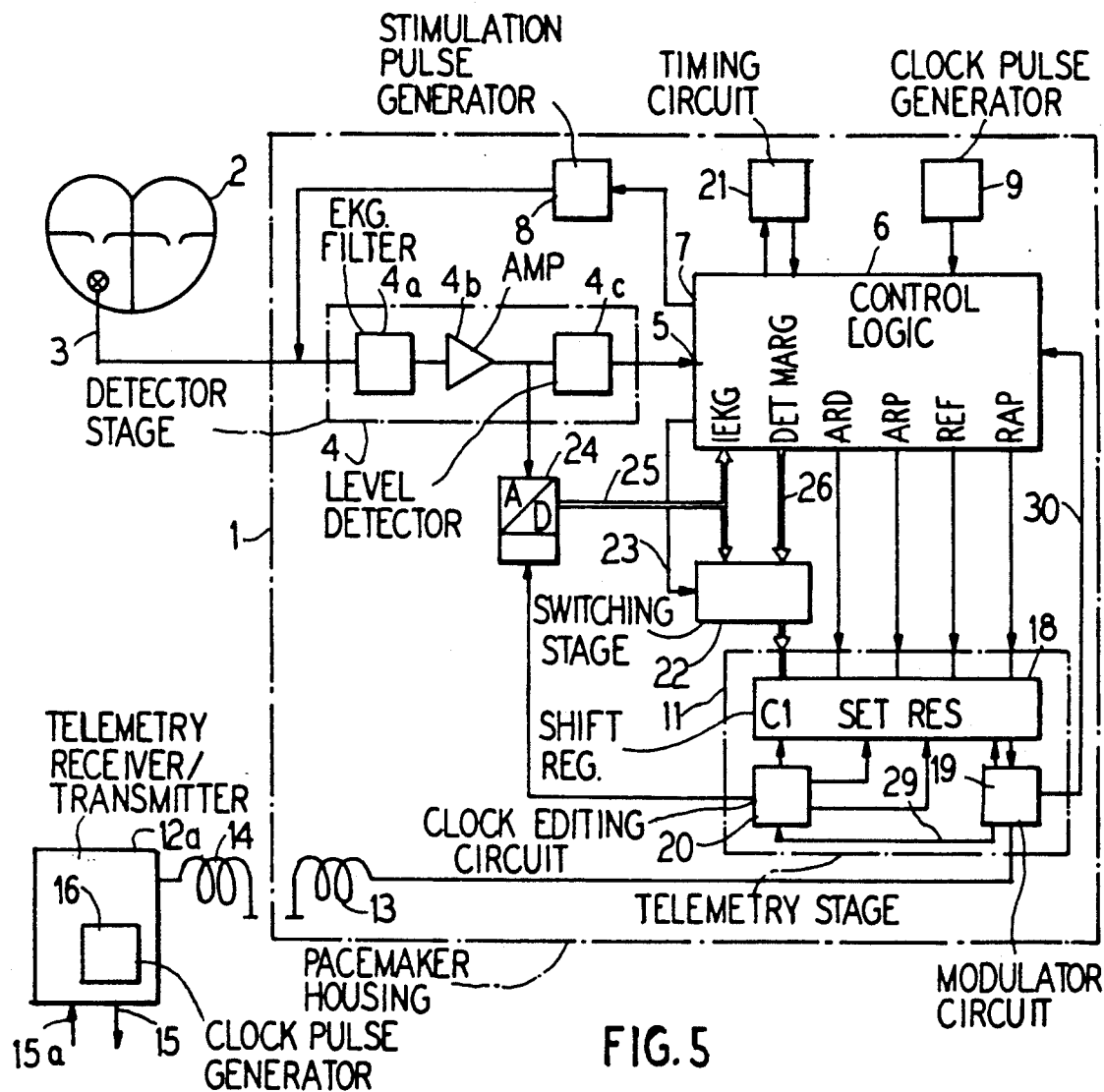

In the embodiment of FIG. 1, a separate clock generator 16 has been shown which activates the telemetry stage 11 for data transmission. As shown in FIG. 4 function of the clock generator 16, may be undertaken by the clock generator 9 allocated to the control logic 6 if the signal from the clock generator 9 is edited in a suitable fashion in the clock editing circuit 20 of the telemetry stage 11. In instances wherein a bi-directional data transmission occurs between the pacemaker housing 1 and the receiver 12, which is the case for programmable heart pacemakers, it is also possible for the clock generator which activates the telemetry stage 11 to be situated in and external receiver/transmitter 12a, as shown in FIG. 5. The clock signals for activating the telemetry stage 11 are then being telemetrically transmitted to the modulator circuit 19 in the telemetry stage 11, which in turn supplies the clock signals to the clock editing circuit 20. In this case, the control logic 6 can be telemetrically supplied on level 30 with signals which cause the actuation of the switching stage 22. In this embodiment the telemetry receiver/transmitter 12a has an input 15a, as well as an output 15.

The data intended for telemetric transmission have been described in connection with the above embodiment for exemplary purposes only, and it will be understood by those skilled in the art that further data may also, or alternative, be transmitted. Moreover, the explanation of the inventive concept disclosed herein has been made using a heart pacemaker as an example, however, it has applicability to any type of implantable medical device.

Although further modifications may be apparent to those skilled in the art, it is the intention of the inventors to embody within the patent warranted hereon all changes and modifications as reasonably and properly come within the scope of their contribution to the art.

We claim as our invention:

1. A medical device comprising:
   therapeutic means adapted for physiologically interacting with a patient;
   control logic means connected to said therapeutic means for monitoring and controlling the operation of said therapeutic means, said control logic means having outputs for delivering data corresponding to a series of momentary logic states defining the operation of said control logic means;
   said therapeutic means and said control logic means being contained in a housing adapted for implantation in said patient;
   data acquisition means connected to said outputs of said control logic means for gaining access to data from said logic means corresponding to a logic state of said control logic means and including means for continuously transmitting said data from a location in said patient to the exterior of said patient; and
   clock generator means for enabling access to said data repeatedly at successive points in time and for activating transmission of data from said logic means to said data acquisition means at said points in time.

2. A medical device as claimed in claim 1 wherein said control logic means is a means for operating said therapeutic means through successive device cycles, and wherein said clock generator means is a means for multiply activating transmission of said current data during a device cycle.

3. A medical device as claimed in claim 1 wherein said clock generator means is contained in said housing adapted for implantation is said patient with said therapeutic means and said control logic means.

4. A medical device as claimed in claim 1 wherein said means for continuously transmitting said data is a means for continuously serially transmitting said data.

5. A medical device as claimed in claim 1 wherein said therapeutic means comprises means for detecting physiological electrical events in a heart and means for electrically stimulating physiological events in said heart.

6. A medical device as claimed in claim 1 further comprising:
   means adapted for implantation in said patient for generating an electrical signal corresponding to a physiological event within said patient;
   means connected to said data acquisition means for converting said electrical signal into logic data; and
   said means for continuously transmitting said data corresponding to a logic state of said control logic including means for simultaneously continuously transmitting said logic data corresponding to said electrical signal.

7. A medical device as claimed in claim 6 further comprising:
   means for combining said logic data corresponding to said electrical signal with said data corresponding to a logic state of said control logic into a single data word, and wherein said means for continuously transmitting said data is a means for continuously transmitting said single data word.

8. A medical device as claimed in claim 1 further comprising:

means connected to said means for acquiring data for generating logic data dependent on the operation of said therapeutic means, and wherein said means for continuously transmitting said data corresponding to a logic state of said logic includes means for simultaneously transmitting said logic data dependent on the operation of said therapeutic means.

9. A medical device as claimed in claim 8 further comprising:

means for combining said logic data dependent on the operation of said therapeutic means with said data corresponding to a logic state of said control logic into a single data word, and wherein said means for continuously transmitting said data is a means for continuously transmitting said single data word.

* * * * *